US00PP35744P2

(12) United States Plant Patent
Hansen

(10) Patent No.: US PP35,744 P2
(45) Date of Patent: Apr. 9, 2024

(54) ***HEUCHERA* PLANT NAMED 'PISTACHIO AMBROSIA'**

(50) Latin Name: ***Heuchera* hybrid**
Varietal Denomination: Pistachio Ambrosia

(71) Applicant: Hans A Hansen, Zeeland, MI (US)

(72) Inventor: Hans A Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 0 days.

(21) Appl. No.: 17/803,768

(22) Filed: Nov. 16, 2022

(51) Int. Cl.
*A01H 6/80* (2018.01)
*A01H 5/02* (2018.01)

(52) U.S. Cl.
USPC ..... Plt./440

(58) Field of Classification Search
USPC ..... Plt./263.1, 440
See application file for complete search history.

*Primary Examiner* — Karen M Redden

(57) ABSTRACT

The new and distinct hybrid of *Heuchera* plant named 'Pretty Pistachio' with foliage of yellowish lime green in summer. The new plant has light pink flowers on densely-branched panicles well above the foliage starting mid-summer and continuing with new panicles until frost. The new plant is vigorous, and produces large clumps, and is useful in the landscape, in containers, or as cut flowers.

2 Drawing Sheets

Botanical denomination: *Heuchera* hybrid.
Variety denomination: 'Pistachio Ambrosia'.

STATEMENT REGARDING PRIOR DISCLOSURES UNDER 37 CFR 1.77(b)(6)

The first public information of the claimed plant, in the form of a non-enabling photograph and brief description, was on a website operated by Walters Gardens, Inc. first accessible on Dec. 1, 2021. This was followed by a small photograph and brief description in the "Walters Gardens 2022-2023 Catalog." Walters Gardens, Inc. obtained the new plant and all information about the new plant from the inventor. No plants of *Heuchera* 'Pistachio Ambrosia' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of Coral Bells in the Saxifragaceae family and given the cultivar name of 'Pistachio Ambrosia'. *Heuchera* 'Pistachio Ambrosia' was hybridized by the inventor on Apr. 24, 2013, at a wholesale perennial nursery in Zeeland, Michigan, USA. The seed or female parent was *Heuchera* 'Citronelle' U.S. Plant Pat. No. 17,934 and the pollen or male parent was 'Coral Forest' (not patented).

*Heuchera* 'Pistachio Ambrosia' was first selected in the fall of 2014 from among thousands of other seedlings from the same cross and hundreds of other crosses and assigned the breeder code 13-789-16. *Heuchera* 'Pistachio Ambrosia' has been asexually propagated by basal cuttings at the same nursery in Zeeland, MI in 2018 and by careful shoot tip tissue culture propagation, and the resultant plants have remained stable and continued to exhibit the same characteristics as the original plant for multiple generations.

BRIEF SUMMARY OF THE INVENTION

The female parent has yellow to chartreuse foliage and shorter flower panicles with creamy-colored flowers. The male has solid deep-green foliage with rose-red flowers.

The nearest comparison cultivars known to the inventor include: 'Pistache' U.S. Plant Pat. No. 19,585, 'Pretty Pistachio' U.S. Plant Pat. No. 29,361, 'Electric Lime' U.S. Plant Pat. No. 21,872, 'Lemon Love' U.S. Plant Pat. No. 31,223, 'Lime Marmalade' U.S. Plant Pat. No. 21,861, and 'Tara' (not patented).

In comparison to the new plant, 'Pistache' has foliage that is similar in color but has more angular acute leaf lobes and the flowers are cream-colored. 'Pretty Pistachio' has foliage that is chartreuse in the spring becoming lime green in the summer, and the flowers of a medium pink are on highly branched panicles produced mid-summer through frost. 'Electric Lime' has smaller foliage with nearly similar color, but the lobes of are more acute, and the flowers are white rather than light pink. 'Lemon Love' has more undulated foliage of chartreuse and the panicles are shorter with creamy-colored foliage. 'Lime Marmalade' smaller and more ruffled lime-green foliage with white flowers. 'Tara' has golden foliage with reddish coloring between the vein earlier in the season and the flowers are near white.

*Heuchera* 'Pistachio Ambrosia' differs from its parents as well as all other coral bells known to the applicant in the following combined traits:

1. The large cordate leaf blades are yellowish lime green in summer with both surfaces matte;
2. Produces light pink flowers with pink calyxes beginning early summer and lasting until frost in the fall;
3. Panicles are dense with flowers rising well above the foliage;

4. Produces large clumps and many large, mostly flat leaves.
5. Plant is vigorous and shows some resistance to leaf burn from the sun.

BRIEF DESCRIPTION OF THE DRAWINGS

The photographs of the new plant demonstrate the overall appearance of the plant including the unique traits. The colors are as accurate as reasonably possible with modern color reproductions. Some slight variations of color may occur as a result of lighting quality, intensity, wavelength, and direction or reflection.

DETAILED BOTANICAL DESCRIPTION

Figure 1:
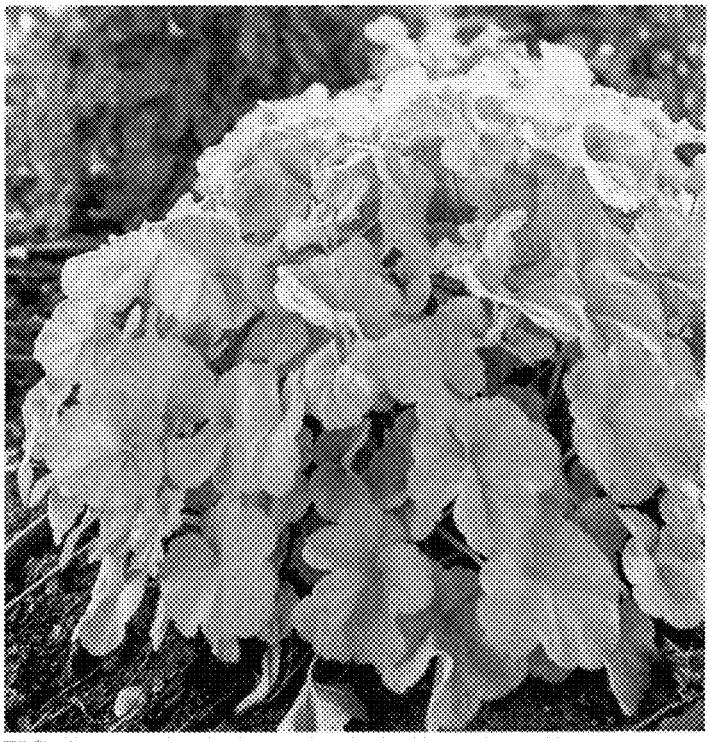
FIG. 1 shows a two-year-old plant in a partially shaded garden prior to flowering.
Figure 2:
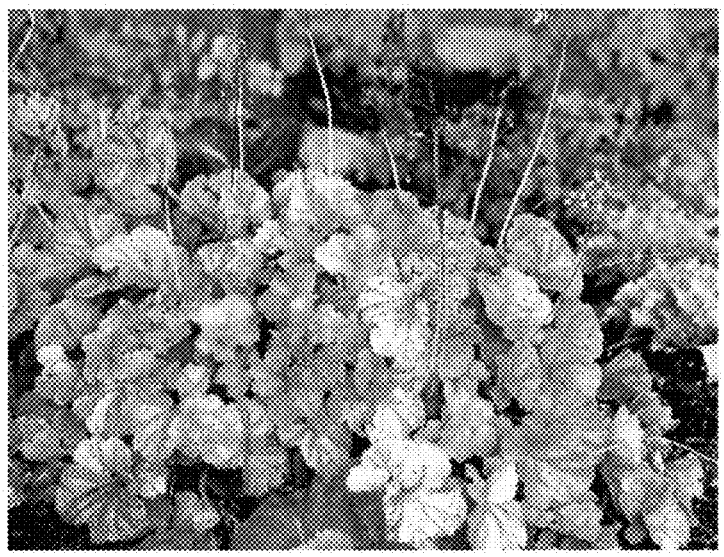
FIG. 2 shows a two-year-old plant in a partially shaded garden mid-season.
Figure 3:
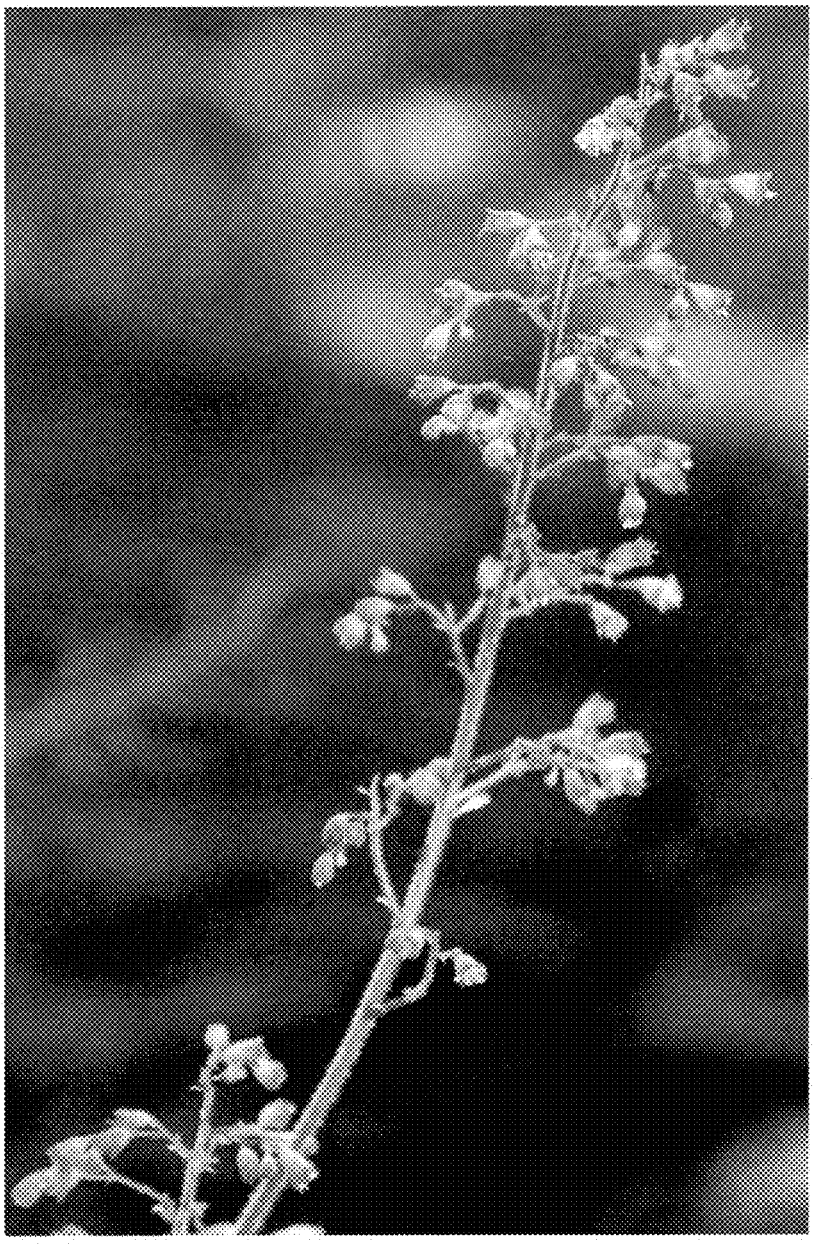
FIG. 3 shows a close-up of the flowers and buds.

The following description is based on two-year-old plants grown in a partially shaded display garden and one-year-old plants grown in a partially shaded greenhouse in Zeeland, Michigan, USA. The new plant has not been grown under all possible environments and may phenotypically appear different under different conditions such as light, temperatures, fertilizer, and water, without any difference in genotype. The color descriptions used are from the 2015 edition of The Royal Horticultural Society Colour Chart except where common dictionary terms are used.

Parentage: Female or seed parent was 'Citronelle' and the pollen or male parent was 'Coral Forest';

Plant habit: Hardy herbaceous perennial with basal rosette of foliage; mounded foliage about 28 cm tall and 65 cm in diameter with upright scapes to about 43 cm long; stems to about 3.5 cm long and 1.3 cm diameter at base with about 12 to 16 leaves per stem and 18 main stems per plant;

Roots: Fibrous, finely branched;

Growth rate: Rapid, rooting from cutting in two weeks and finishing in three-liter container in about 3 months;

Foliage: Cordate; sparsely hirsutulous adaxial and abaxial; palmately shallowly lobed with five to seven main lobes dissected less than one-quarter the way to petiole or midrib; apex and lobes rounded, base cordate to auriculate with basal lobes frequently overlapping about 3 cm; margins crenate to mucronate, ciliolate; slightly lustrous adaxial becoming matte adaxial and matte abaxial; held nearly horizontal; marginal undulation moderate;

Leaf blade size: To about 130 mm long and 128 mm wide, average about 105 mm long and 102 mm wide;

Leaf color: Spring and young emerging leaves adaxial between RHS 143A and RHS 146D and with no silver or dark green marbling surrounding the veins, spring young emerging leaves abaxial between RHS 147B and RHS 147C; mature mid-season leaves adaxial variable with some leaves with portions nearest RHS 19D, RHS 146B, and RHS 146D, with no marbling of silver or darker green surrounding the veins, abaxial mature mid-season leaves variable with some leaves with portions between RHS 147C and RHS 148C and other portions nearest RHS 158B; deciduous with no winter color;

Leaf quantity: Dense, about 140 per plant;

Veins: Palmate; puberulent adaxial and hirsutulous to pubescent abaxial; nearly flat adaxial and costate abaxial;

Vein color: On emerging or early spring foliage adaxial nearest RHS N144D with emerging or early spring abaxial between RHS 147D and RHS 194C; mid-season and flowering time adaxial variable, random portions nearest RHS 19D, RHS 147C, and RHS 146D, mid-season and flowering time abaxial between RHS 147D and RHS 194D;

Petiole: Terete; pubescent with hairs to about 2 mm long; with base amplexicaul; to about 24 cm long and 3.5 mm diameter just above stipule; average about 19 cm long and about 3 mm diameter above stipule and 7 mm across at base including stipule;

Petiole color: Emerging leaf nearest RHS 145B; mature leaf nearest RHS 146D;

Stipule: At base of petiole, about 7 mm long and about 7 cm wide at base; with an acute apex on both sides; truncate base; ciliolate margin;

Stipule color: Adaxial and abaxial between RHS 147D and RHS 145D;

Peduncle: About 46 per plant throughout the growing season; panicle; terete; stiff; pubescent; upright; to about 43 cm long and 5 mm diameter at base, average about 40 cm tall and about 4.5 mm diameter; about ten per plant with up to 150 flowers per panicle, average about 130; heavily-branched panicle with up to 18 branches per peduncle up to about 7 cm long and about 1 mm diameter decreasing distally, average 15 branches per panicle; branches outwardly to slightly upright; flower density moderate;

Flowering longevity: Panicle effective for about six to nine weeks;

Peduncle color: Young developing or lower portion and more shaded between RHS 145C and RHS 146D distally becoming moderately blushed with nearest RHS 183B; mature lower portion nearest RHS 146D and distally becoming nearest RHS N144A with a moderate blush of nearest RHS 187C;

Pedicel: Terete; finely puberulent; about 2 mm long and 0.5 mm diameter; aspect slightly drooping;

Pedicel color: Nearest RHS 185B;

Buds one day prior to opening: Ellipsoid; rounded apex and rounded base; puberulent to glandular; about 5.5 mm long and 2.5 mm diameter;

Bud color one day prior to opening: Proximal portion between RHS 185D and RHS 181D, distal two-thirds nearest RHS 153B;

Flower: Perfect; complete; campanulate; actinomorphic; about 6 mm long to exserted style and 3.5 mm in diameter at face; individual flowers lasting about 4 days on plant or as cut flower; persistent;

Flower aspect: Slightly downwardly to outwardly;

Calyx: Base fused in proximal 4.5 mm to form hypanthium; pubescent abaxial; glabrous adaxial; about 5.5 mm long and 3.5 mm wide; persistent;

Sepal: Five; apex acute; fused in basal 4.5 mm; free in distal 1 mm;

Sepal color: Adaxial margin between RHS 53A and RHS 53B; proximally nearest RHS 55D; abaxial base between RHS 53D and RHS 52C and distally between RHS 53C and RHS 53B and RHS 53A at apex; darkening to between RHS 53A to RHS 53B with age.

Petals: Five; spatulate; acute apex and attenuate base; margin entire, glabrous abaxial and adaxial; about 2 mm long and 1 mm wide in middle;

Petal color: Abaxial and adaxial nearest RHS 55D;

Androecium: Five; adnate to adaxial calyx about 1.5 mm above base;

*Filaments*.—Five, thin, glabrous; about 1.5 mm long and less than 0.3 mm diameter; color nearest RHS 55D.

*Anthers*.—Ellipsoidal; distinct; basifixed; longitudinal; color nearest RHS N155C.

*Pollen*.—Not observed.

Gynoecium: One; two-beaked; half-inferior; bifid style with pistil split at ovary; 6 mm long;

*Style*.—Bifid; split apart at apex of ovary; about 4.5 mm long and about 1 mm diameter; color nearest RHS 145C proximal 1 mm and distally nearest RHS 155C.

*Stigma*.—Acute apex; about 0.1 mm diameter; color nearest RHS NN155B.

*Ovary*.—Half-inferior; about 2.5 mm long and 2 mm diameter; ellipsoidal to globose; base rounded; color nearest RHS 150D.

Fruit: Two-beaked ellipsoidal capsule; about 6 mm long and 3 mm across; color nearest RHS 200B;

Seed: Thin ellipsoidal; less than 1 mm long and less than 0.5 mm wide; color between RHS 202A and RHS 200A;

Growth: The new plant grows best with ample moisture and drainage in either sun or shade and is winter hardy from USDA zones 4 to 9.

Disease and pest tolerance: The new plant is less prone to leaf burn or discoloration from the sun than 'Pretty Pistachio'. Other resistance and tolerance outside of that normal for *Heuchera* is not known.

It is claimed:

1. The new and distinct coral bells plant named *Heuchera* 'Pistachio Ambrosia' as herein described and illustrated.

* * * * *